US009589373B2

(12) United States Patent
Gindele

(10) Patent No.: US 9,589,373 B2
(45) Date of Patent: Mar. 7, 2017

(54) MONTE CARLO MODELING OF FIELD ANGLE-DEPENDENT SPECTRA FOR RADIOGRAPHIC IMAGING SYSTEMS

(71) Applicant: Carestream Health, Inc., Rochester, NY (US)

(72) Inventor: Edward B. Gindele, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 356 days.

(21) Appl. No.: 14/172,345

(22) Filed: Feb. 4, 2014

(65) Prior Publication Data
US 2014/0218362 A1  Aug. 7, 2014

Related U.S. Application Data

(60) Provisional application No. 61/760,831, filed on Feb. 5, 2013.

(51) Int. Cl.
G06T 7/00 (2006.01)
G06T 11/00 (2006.01)
A61B 6/03 (2006.01)
A61B 6/00 (2006.01)

(52) U.S. Cl.
CPC ............ G06T 11/006 (2013.01); A61B 6/032 (2013.01); A61B 6/4291 (2013.01); A61B 6/482 (2013.01);
(Continued)

(58) Field of Classification Search
CPC ......... G06T 11/005; G06T 2207/10116; G06T 2211/424; G06T 5/50; G06T 5/002;
(Continued)

(56) References Cited

U.S. PATENT DOCUMENTS 5,090,040 A * 2/1992 Lanza ................... A61B 6/505
378/162
7,065,234 B2 * 6/2006 Du ........................ G06T 11/005
382/131
(Continued)

OTHER PUBLICATIONS

Sisniega, Alejandro, et al. "Automatic Monte-Carlo Based Scatter Correction for X-ray cone-beam CT using general purpose graphic processing units (GP-GPU): A feasibility study." Nuclear Science Symposium and Medical Imaging Conference (NSS/MIC), 2011 IEEE. IEEE, 2011.*

(Continued)

*Primary Examiner* — Sultana M Zalalee

(57) ABSTRACT

Methods and/or apparatus for iteratively reconstructing a 3-dimensional volume for an object captured with radiographic imaging that includes an electronic sensor, exemplary methods can be performed at least in part on a computer, can include receiving a 3-dimensional volume data set generated from imaging an object; identifying a set of intra system components corresponding to system components used to capture images of the object, where the intra system components include at least an x-ray source within system components configured to be placed before the object; representing x-ray emission characteristics of the x-ray source as a function of angle and energy; using the 3D emission characteristics to simulate the forward projection of x-ray photons to generate a primary image and/or a scattered image; and using the primary image and/or the scattered image to reconstruct an improved 3-dimensional volume data set.

20 Claims, 15 Drawing Sheets

(52) U.S. Cl.
CPC ............ *A61B 6/483* (2013.01); *A61B 6/5205* (2013.01); *A61B 6/5258* (2013.01); *A61B 6/5282* (2013.01); *G06T 2211/408* (2013.01); *G06T 2211/424* (2013.01)

(58) Field of Classification Search
CPC . G06T 2207/10081; G06T 2207/20224; G06T 2207/30004; G06T 5/003; G06T 7/0016; G06T 2207/10072; G06T 2207/10084; G06T 2211/408; G06T 2211/421; A61B 6/032; A61B 6/5282; A61B 6/027; A61B 6/4291; A61B 6/482; A61B 6/583; A61B 6/4035; A61B 6/4085; A61B 6/00; A61B 6/466; A61B 6/541; A61B 5/0095; A61B 5/02007; A61B 5/0456; A61B 5/7232; A61B 5/7257
See application file for complete search history.

(56) References Cited

U.S. PATENT DOCUMENTS

| | | | | |
|---|---|---|---|---|
| 2006/0140340 A1* | 6/2006 | Kravis | ................... | G01N 23/20 378/57 |
| 2009/0290682 A1* | 11/2009 | Star-Lack | ............. | G06T 11/005 378/87 |
| 2010/0014730 A1* | 1/2010 | Hahn | ........................ | G06T 5/50 382/131 |
| 2010/0027867 A1* | 2/2010 | Bernhardt | ................ | A61B 6/00 382/132 |
| 2013/0004042 A1* | 1/2013 | Yang | ..................... | G06T 11/005 382/131 |

OTHER PUBLICATIONS

J. H. Siewerdsen, et al., "Spektr: A computational tool for X-ray spectral analysis and imaging system optimization", Medical Physics 3 1, pp. 3057-3067, (2004).*

Day, G. J., and D. R. Dance. "X-ray transmission formula for antiscatter grids." Physics in medicine and biology 28.12 (1983): 1429.*

F. Salvat, J.M. Fernandez-Varea and J. Sempau, PENELOPE—2008: A Code System for Monte Carlo Simulation of Electron and Photon Transport. Workshop Proceedings Barcelona, Spain Jun. 30-Jul. 3, 2008.*

Mail, N., et al. "The influence of bowtie filtration on cone-beam CT image quality." Medical Physics 36.1 (2009): 22-32.*

\* cited by examiner

MONTE CARLO MODELING OF FIELD ANGLE-DEPENDENT SPECTRA FOR RADIOGRAPHIC IMAGING SYSTEMS

CROSS REFERENCE TO RELATED APPLICATIONS

This application claims the benefit of earlier filed commonly assigned, U.S. patent application Ser. No. 61/760,831, filed Feb. 5, 2013, entitled "MONTE CARLO MODELING OF FIELD ANGLE-DEPENDENT SPECTRA FOR X-RAY IMAGING SYSTEMS", in the name of Edward B. Gindele, which is incorporated herein by reference in its entirety.

FIELD OF THE INVENTION

The invention relates generally to radiographic imaging systems. More specifically, the invention relates to volumetric X-ray imaging systems and/or methods for using the same.

BACKGROUND OF THE INVENTION

With digital radiography, the radiation image exposures captured on radiation-sensitive layers in X-ray imaging panels are converted to electronic image data which is then stored in memory circuitry for subsequent read-out and display on suitable electronic image display devices. Monte Carlo simulation tools are well known to assist, modify or be calculate volumetric or 3D representations of imaged objects (e.g., radiographic imaged objects). However, the computational resources to operate such tools to model discrete components of radiographic imaging systems have heretofore severely restricted the deployment of such tools for volumetric radiographic imaging.

SUMMARY OF THE INVENTION

An aspect of this application is to advance the art of radiography imaging systems.

Another aspect of this application to address in whole or in part, at least the foregoing and other deficiencies in the related art.

It is another aspect of this application to provide in whole or in part, at least the advantages described herein.

Another aspect of the application is to provide methods and/or apparatus by which radiographic imaging systems and/or methods can include Monte Carlo simulation of radiographic imaging systems.

Another aspect of the application is to provide imaging method and/or apparatus embodiments by which Monte Carlo representations can assist, modify or calculate operations to generate the reconstruction of two-dimensional and three-dimensional radiographic images.

In accordance with one embodiment, the present invention can provide a method of iteratively reconstructing a 3-dimensional volume for an object captured with an x-ray imaging system, including a) receiving a 3-dimensional volume data set generated from imaging an object; b) identifying a set of intra system components corresponding to system components used to capture images of the object, where the intra system components include system components placed between the x-ray source of emission and the object; c) constructing a bounding spectral curve as a function of photon energy by (i) calculating the transmission value through the intra system components for a multiplicity of photon emission ray paths configured to intercept a sensor, and (ii) using the multiplicity of photon emission ray paths transmission values to construct the value of the bounding spectral curve; d) generating a scattered image using the bounding spectral curve by accepting or rejecting simulated photons; and e) using the scattered image to reconstruct an improved 3-dimensional volume data set.

In accordance with one embodiment, the present invention can provide a method of iteratively reconstructing a 3-dimensional volume for an object captured with an x-ray imaging system including receiving a 3-dimensional volume data set generated from imaging an object; identifying a set of intra system components corresponding to system components used to capture images of the object, where the intra system components include at least an x-ray source within system components configured to be placed before the object; representing x-ray emission characteristics of the x-ray source as a function of angle and energy; using the 3D emission characteristics to simulate the forward projection of x-ray photons within the object to generate a primary image and/or a scattered image; and using the primary image and/or the scattered image to reconstruct an improved 3-dimensional volume data set.

In accordance with one embodiment, the present invention can provide a method of iteratively reconstructing a 3-dimensional volume for an object captured with an x-ray imaging system that includes an electronic sensor, the method performed at least in part on a computer including receiving a 3-dimensional volume data set generated from imaging an object; identifying a set of intra system components corresponding to system components used to capture images of the object, where the intra system components include system components placed between the x-ray source of emission and the object; constructing a bounding spectral curve relating to the intra system components, where the bounding spectral curve is constructed as a function of photon energy by calculating the transmission value through the intra system components for a multiplicity of photon emission ray paths intercepting the sensor, and selecting the maximum transmission value for the multiplicity of photon emission ray paths; using the bounding spectral curve to simulate the forward projection of x-ray photons within the object to generate a primary image and/or a scattered image; and using the scattered image to reconstruct an improved 3-dimensional volume data set.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DESCRIPTION OF EXEMPLARY EMBODIMENTS

Figure 1:
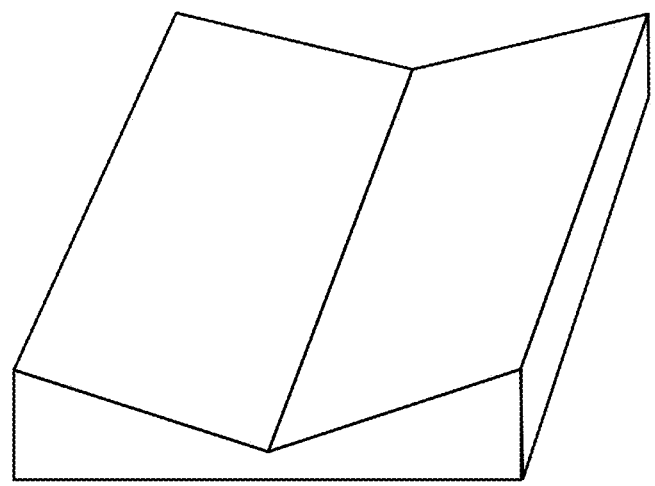
FIG. 1 is a diagram that shows an exemplary generalized bow-tie filter with a ramp-function, cross section symmetric about the center line.

The following is a description of exemplary embodiments according to the application, reference being made to the drawings in which the same reference numerals identify the same elements of structure in each of the several figures, and similar descriptions concerning components and arrangement or interaction of components already described are omitted. Where they are used, the terms "first", "second", and so on, do not necessarily denote any ordinal or priority relation, but may simply be used to more clearly distinguish one element from another.

The photon spectrum for X-ray capture systems is a function of the emission field angle. Spectrum variability is the most pronounced for cone-beam computed tomography (CBCT) systems with wide field angles operating close to the anode angle limit. Filtration devices also contribute to the change in the photon spectrum with an emission field angle, especially for variable-thickness filters, e.g., how-tie filters. The change in the photon spectrum is primarily due to the distance traversed through the anode and filtration materials with emission field angles. Although Monte Carlo X-ray simulations can include the materials and geometries for these source assembly elements, the computational requirements are considered prohibitive. As a consequence, X-ray Monte Carlo simulation implementations ignore emission field angle spectral effects. Our approach uses a probabilistic rejection scheme to model the emission field angle spectral effects within the context of a Monte Carlo simulation tool. A bounding spectrum is constructed that supersedes all possible spectrums, i.e., for all emission field angles. Photons are generated with the bounding spectrum and rejected or accepted based on the probability of transmission through the cascade of anode and filtration materials relative to a pre-calculated maximum probability of transmission. The resultant photon spectrum properly models the intensity and spectral shape of the emitted photons as a function of the emission field angle. The modeling accuracy improvement over the constant spectrum approximation was calculated for a CBCT system for anode voltages ranging from 50 Kvp to 110 Kvp. The maximum improvement in predicted primary and scatter signals was approximately 5% for a system configuration employing a simple filtration and 25% for a CBCT system employing a bow-tie filter with less than a 10% additional computation cost.

For decades, Monte Carlo simulation tools have been used to analyze X-ray imaging capture systems, particularly for analyzing X-ray scattering. The physical mechanisms of X-ray scattering are well understood. In practice, it is the complicated geometry and distribution of material in the path of the X-rays that make the effects of scattering difficult to predict. Monte Carlo analysis is especially useful for predicting the spatial pattern of X-ray radiation resulting from scattering events. This is principally due to the fact that the mechanisms of scattering events can be described mathematically, and current computer implementations have enough memory to represent the spatial distribution of material for complex objects. With these two essential attributes incorporated, Monte Carlo simulation tools have the potential to accurately model X-ray imaging-capture systems. The last necessary requirement for practical Monte Carlo simulation tools is computational horsepower. It simply takes an enormous number of simulated photons to produce images of useful quality.

It is well recognized that the X-ray spectrum of cone-beam computed tomography (CBCT) systems varies with emission field angle. The spectrum of X-ray photons, both the intensity and spectral shape, vary significantly as the photons emerge from the anode surface. The heel-effect reduction in output intensity is the most pronounced observable evidence. This is principally due to the variation in anode material thickness experienced by photons emitted at different angles. The most common components used to shape the spectrum are parallel plate filters. CBCT systems often employ higher field angles than other X-ray capture systems. It is not unusual for a CBCT system to have a maximum emission field angle of 20°, which implies a 6% greater filtration thickness for the corner of the field relative to the center. The magnitude of the spectral effect depends on the magnitude of the photon energy transmittance. For a center transmittance of 0.25, a 6% change in thickness translates to an 8% change in corner transmittance.

The algorithm presented here was motivated by the goal of developing a practical implementation of an accurate X-ray scatter-estimation component for a CBCT system within the context of an iterative reconstruction algorithm. X-ray scatter is widely recognized as a major confounding factor for accurate reconstruction values produced by CBCT systems. A Monte Carlo approach was chosen, and the publicly available MC-GPU software implementation was used as a framework. Modeling additions, including source spectrum, filtration, attenuation to material and density conversion, and detector response function, were added to the implementation to improve the accuracy and provide the ability to model the specifics of a particular set of hardware. The primary motivation behind the development of the field angle-dependent spectral feature was the need to model bow-tie filters. Bow-tie filters are designed specifically to reduce X-ray beam intensities for greater emission field angles. As the thickness of a bow-tie filter varies with the emission field angle, so does the emergent X-ray photon spectrum.

Monte Carlo X-ray simulation implementations model the source spectrum by a one-dimensional (1-D) function of the photon energy independent of the thickness of filtration material and, thus, independent of the emission field angle. In reality, the filtration thickness varies with the emission field angle, and the photon spectrum also varies with the emission field angle.

1.1 Inverse Function Method

The most common method for generating random photon energies that conform to a prescribed probability distribution is the inverse function method. First, a cumulative probability density function (PDF) is constructed from the photon emission probability distribution function (pdf), F(E). Next, the inverse function of the cumulative PDF can be used to randomly generate photon energies. In equation (1) the integral expression represents the cumulative PDF of F(E). The inverse cumulative PDF $\Phi(\rho)$ will generate photon energies from uniform random numbers ($\rho$ ranging from 0 to 1).

$$\Phi(\rho) = \{\int_0^\gamma F(E)dE\}^{-1} \quad (1)$$

1.2 Rejection Method

A random sampling of a complex distribution is sometimes more easily generated using the rejection sampling method.[3] In this approach, it is assumed that a final distribution P(E) is functionally the product of two or more functions, e.g., $$P(E)=R(E)S(E). \quad (2)$$

Random samples are generated using the inverse function method for one function, e.g., S(E), with resultant samples accepted or rejected in evaluation of the rejection function R(E). The classic illustrative example of the rejection method is the problem of generating random samples from a unit circle. In the first step, a uniform random value is sampled independently for the x and y coordinates (corresponding to the probability function S(E)). In the second step, the coordinate pair (x,y) is evaluated to be either inside or outside of the circle. When the selected point is outside the circle, the sample is rejected. When the selected point is inside the circle, the sample is accepted.

As long as S(E)>R(E) for all E, the distribution of accepted samples will conform to the probabilities of P(E). PENELOPE uses the rejection sampling method extensively for generating the angular distribution of both Compton and Rayleigh scattering events.

1.3 Spectrum Modeling Options

For a general case, the pdf of the X-ray source energy emission (S) is a function of the photon energy (E), the polar angle (θ), and the azimuth angle (φ) (with the origin located at the anode surface). However, the source pdf can be represented as:

$$S(E,\theta,\phi)=A(E,\theta,\phi)F(E,\theta,\phi), \quad (3)$$

where the function A( ) represents the emission characteristics of the anode material, and F( ) represents the spectral transmission probabilities of the filtration. However, the angular dependence of the anode emission can be modeled as distributed spherically uniform and traversing through a variable thickness of anode material as a function of the angle. Therefore, the anode thickness angular dependence can be incorporated into the filtration function.

There are multiple approaches that can be used to model the angle dependency of the source spectrum. The most accurate approach is to include the materials and geometry of the anode and filters within the Monte Carlo simulation code. Unfortunately, this is also the most computationally intensive approach. Alternatively, the electron beam, electron transport, and resulting Bremsstrahlung radiation can be approximated by an anode emission function A(E) with uniform hemispherical angular distribution. The X-ray photon point of emission can be approximated as taking place at a finite depth within the anode material. The filtration material properties and geometry, i.e., location, thickness, etc., can also be included in the Monte Carlo simulation. Unfortunately, very few photons emitted within the anode material will make it through the last filter. This is, in part, due to the high coefficient of absorption for typical filtration materials. As a consequence, the processing is very inefficient for generating imaging photons with the prescribed energy distribution. However, this approach is useful for determining the spectrum of the emerging photons from the source/filtration subassembly.

Although most inverse PDF implementations of random variables involve 1-D functions, it is possible to construct an implementation for the 3-dimensional (3-D) source emission function described above. The source function $S(E, \theta, \phi)$ can be evaluated at a set of discrete values for each of the three variables, $S(E_i, \theta_j, \phi_k)$, and then assembled into a sequence of probability values (q):

$$S(q)=S\{s_1,s_2,\ldots,s_n\}. \quad (4)$$

where the variable q corresponds to a unique combination of i, j, k indices for the discretized function $S(E_i, \theta_j, \phi_k)$.

With the 3-D function $S(E, \theta, \phi)$ reduced to a serialized 1-D function S(q), a cumulative probability distribution function can be constructed by the inverse function method described above. The main advantage of this approach is the simplicity of the construction. Operationally, the execution speed of this approach should be fast for CPU-based implementations since it only involves a lookup table. The main drawback of this approach is the relatively large amount of memory required for the data tables to store the sampling function with enough fidelity. For a typical implementation, the tables can require on the order of $10^7$ to $10^9$ elements. Secondarily, the 3-D inverse approach suffers from discretization, i.e., the resultant source photon samples are generated with discrete angular samples, and they are not easily interpolated because of the serialization feature.

A simple rejection scheme can be implemented using (3). In this approach, an inverse cumulative PDF is constructed just for the anode spectral emission function A(E). A first random number is selected and used to determine the sampled value for E. Next, two uniform random values are used to determine the sampled angular variable values for θ and φ on the unit sphere. The filtration-transmission function F(E, θ, φ) serves as the rejection function. A fourth random number is used to compare with the evaluated filtration-transmission probability, for given values of E, θ, and φ, to accept/reject the sampled variables, E, θ, and φ. Although this approach is simple to implement and has reduced or minimal storage requirements, the percentage of samples rejected is extremely high. For a typical system, less than 0.01% of the generated samples are accepted.

Alternatively, the above rejection scheme can be modified to calculate a weighting factor for each generated photon, based on the calculated filtration-transmission function F(E, θ, φ). With this approach, all of the generated photons are used in the simulation process. However, most of the photons ray traced through the object of interest have very low weight values and therefore do not contribute substantially to the relevant outcome.

2 Exemplary Embodiments

Exemplary embodiments can use a rejection scheme that employs a surrogate X-ray spectrum to generate sample photons as a function of energy E and angles θ and φ and uses a rejection function based on the probability of transmission relative to a maximum or prescribed transmission probability. The source spectrum $S(E, \theta, \phi)$ is assumed to comprise an anode source emission function A(E) and the filtration-transmission function F(E, θ, φ), as described by (3).

A surrogate spectrum S'(E) can be constructed by finding the maximum source spectrum value for any angle $$S'(E)=\max \theta,\phi\{A(E)F(E,\theta,\phi)\} \quad (5)$$

$$\forall \theta, \text{ and } \phi. \quad (6)$$

It should be noted that the surrogate spectrum does not necessarily correspond to a physically realizable spectrum. That is, for a given system, there may be no emission field angle that actually exhibits this spectrum. This may be due to the non-linear nature of the max{ } operator. The surrogate spectrum can be used as an upper bound for the actual source spectrum for every emission field angle. However, for a typical system employing parallel flat plate filters, the surrogate spectrum can be identical to the spectrum corresponding to the minimum transmission distance through the filters. The source sampling function $\Phi(\rho)$ is constructed using the inverse function of the cumulative surrogate spectrum function as given by (7).

$$\Phi(\rho) = \{\int_0^v S'(E)dE\}^{-1} \qquad (7)$$

The rejection function $R(E, \theta, \phi)$ is constructed as the ratio of the transmission function divided by the surrogate spectrum function $$R(E, \theta, \phi) = \frac{A(E)F(E, \theta, \phi)}{S'(E)}, \qquad (8)$$

with the requirement that $$S'(E) \geq A(E)F(E, \theta, \phi) \qquad (9)$$

$$\forall E, \theta, \text{ and } \phi. \qquad (10)$$

Operationally, the variables $\theta_s$ and $\phi_s$ are selected using two uniform random numbers sampled from the unit hemisphere. A third random number $\rho$ is used to generate the sampled energy value $E_s$ using the source sampling function $\Phi(\rho)$. A fourth random number issued to evaluate the rejection function value $R(E_s, \theta_s, \phi_s)$ to either accept or reject the sampled variables.

3 Method

The MC-GPU software code version 1.1 was used as a starting point with a number of custom embellishments described below. The MC-GPU Monte Carlo simulator is an adaptation of PENELOPE, which is intended for medical X-ray imaging applications. Translated from Fortran, the MC-GPU software is written in C++ and includes some important practical modifications needed for computational efficiency: (1) objects are described by a rectangular grid of discrete voxels with each voxel being described by a material type and a density value, and (2) X-ray photon transport and three main X-ray interactions are supported by Compton scattering, Rayleigh scattering, and photoelectric absorption, i.e., electron transport and X-ray fluorescence processes are not modeled.

The custom Monte Carlo simulation tool used to generate the results described herein includes the following additional models: (1) source, (2) filtration, (3) grid transmission model, and (4) detector response model. The source and filtration models include angular spectral dependence. The grid and detector models include dependencies on position, photon energy, and angle of incidence.

3.1 CBCT System Parameters

A model of an exemplary orthopedic CBCT system was used for all the simulations. The essential modeling parameters are as follows: source-detector distance 56 cm, source-to-axis distance 43 cm, detector dimensions 29.8 cm×29.8 cm with 768×768 pixels, 1.0 mm acrylic detector cover, inherent filtration 2.0 mm aluminum, additional filtration 0.2 mm copper, anode angle 15°, and source-to-filter distance 3.7 cm. The orthopedic CBCT system can be fitted with an anti-scatter grid, which was modeled with the following parameters: thickness—1.115 mm, height—0.85 mm, ratio—10, frequency—80 lpcm, absorber material—lead, matrix material—polycarbonate, and with no focus error oriented in the horizontal direction. The source assembly and inherent filtration was modeled with a 2° tilt in horizontal direction. The largest emission field angle exhibited is 20.6° for the corner pixels. The edge emission field angles are 14.9°.

3.2 Source Model

The source model includes an anode X-ray emission model that assumes the electron beam penetrates the anode material to an average depth, which is dependent as a function of the applied voltage. The SpekCalc software tool was used to generate the spectral data of the anode X-ray emission as a function of the applied tube voltage (Kvp). For each anode voltage modeled, the anode X-ray emission function was generated by setting the material to tungsten and the anode angle to 90° with no additional filtration. The emission depth was determined by setting the anode angle to 90° with a variable thickness of an additional tungsten filtration. The thickness was varied until a match in the output spectrum was achieved by a spectrum generated with a 30° angle and no additional filtration. As a matter of practicality, a system employing a 15° anode angle and a source/detector 15° of the half-emission field angle will require a tilt of the source assembly away from the cathode to reduce or minimize the extremely low output intensity on the anode side of the detector.

With the above-described source model, the X-ray spectrum, both in intensity and shape, is modeled as a function of polar and azimuth angles. Random angles are selected with an isotropic hemispherical distribution. The rejection criterion is employed thus generating the physically correct distribution of photons. The inherent source filtration (the net effect of the X-rays traveling from the anode surface to the source exit window) is treated as a filter. Similarly, once a randomly selected photon has been accepted, at a given polar and azimuth angle, the transmission losses incurred from traveling through the additional distance of the anode material is also included.

For the angle-independent modeling scenarios, i.e., a constant spectrum approximation, photons are generated from a uniform angular distribution using a spectral emission function. This function is constructed by cascading an anode emission function with a representative filtration-transmission function. The angle-independent modeling scenarios presented used the filtration material thickness as sampled from the source ray taken halfway between the center ray and the corner ray. In the figures presented below, this point is referred to at the midpoint.

3.3 Filtration Model

The inherent filtration for the exemplary orthopedic CBCT system consists of a 2.0 mm aluminum source cover plate. An additional 0.2 mm copper filter is placed to reduce low energy emissions. Both the aluminum and copper plates were modeled as parallel plate filters. The simple filtration imaging examples described below use the inherent plus 0.2 mm copper filters. For the bow-tie imaging examples, the 0.2 mm copper filter is replaced by the bow-tie filter.

There is no standard bow-tie filter design. Most are proprietary designs for which there is no open literature description with regard to the geometry. Occasionally, the material thicknesses for the center and edge are given.

Figure 2:
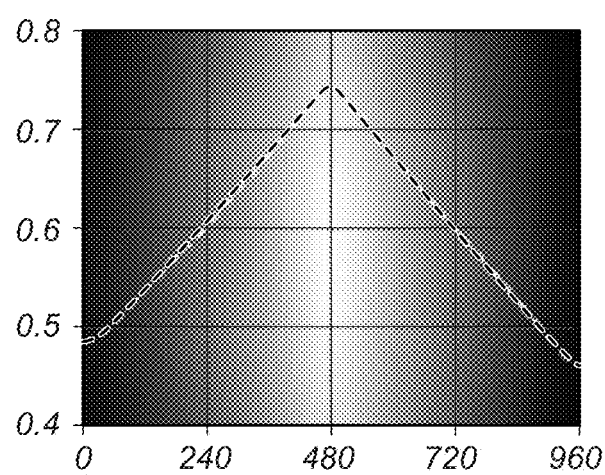
FIG. 2 is a diagram that shows gray scale calibration air image for an orthopedic system modeled with a bow-tie filter and an anode voltage of 90 Kvp.

However, the functional shape of the contour is usually not disclosed. The geometry of a generic copper bow-tie filter (shown in FIG. 1) was modeled as having a constant thickness in the vertical direction and a linearly increasing thickness from the center to the edge in the horizontal direction backed by 1.0 mm of aluminum. The center thickness was set to 0.1 mm and the edge thickness was 0.6 mm with an overall width of 44 mm. The corresponding calibration air image is shown in FIG. 2 as a gray-scale image. The graph overlay shown in FIG. 2 is a horizontal intensity trace taken through the center of the image. The bow-tie filter reduces the source output intensity to less than 0.5 on the anode side of the image. The asymmetry in the graph is due to the greater attenuation on the right side of the detector caused by the anode heel effect.

3.4 Object Model

Two digital phantoms were used to generate the results. The knee phantom was acquired on a fan-beam computed tomography (FBCT) system of a cadaver leg. The head phantom was taken from the publicly available "University of North Carolina Volume Rendering Test Data Set" acquired from a FBCT system of a cadaver. The digital head phantom was edited to remove metal artifacts in 14 of the 109 axial slices.

Voxel-based digital phantoms were used in the simulations captured on the FBCT systems. As such, the inherent scatter of these devices is considerably less than the CBCT system under investigation. The 3-D data sets, input in Hounsfield units (HU), were segmented based on voxel values into material categories: air, soft tissue, adipose, muscle, bone-marrow, and bone with variable density. A nominal density was assumed for each material, and a variable density for each voxel was assigned based on the voxel value. For example, for a voxel with a value of −500, the material assignment was soft tissue with a density of 0.5 g/cm$^3$. Adipose tissue was assigned for voxels ranging from −150 to −40 HU. Soft tissue was assigned from −1000 to −150 HU and from −40 to +10 HU. Muscle was assigned from +10 to +60 HU, and bone marrow was assigned from +60 to +175 HU. The bone was assigned from +175 to +3000 HU with a voxel value of +750 being assigned to the nominal value of bone density. Higher HU values were linearly graduated with a maximum bone density value of 1.5 times the nominal value. Material scattering and attenuation cross-sectional data were generated using the PENELOPE tool box.

3.5 Anti-Scatter Grid Model

The anti-scatter grid model calculates the average photon transmittance over one spatial period as a function of the photon energy, angle of incidence, and pixel position. The grid is assumed to be composed of two materials: an absorber material used for the thin plates (typically lead) and a matrix material (typically aluminum) packed between the absorber plates. The grid is assumed to have a constant spatial frequency of plates, parallel in one direction, focused in the orthogonal direction at a parallel line in space, and with a specified grid ratio. For the simulations conducted here, the anti-scatter grid was assumed to be perfectly focused at the source point of emission.

3.6 Detector Model

The orthopedic prototype CBCT system uses a Varian 3030 (Varian Medical Systems) detector panel. A detector-response curve as a function of photon energy was calculated, using a separate Monte Carlo simulation using a volume of CsI (assuming a packing fraction of 0.75). Modeled as a parallel plate of homogeneous material, the voxel absorption was recorded for the volume accounting for the effects of Compton and Rayleigh scattering, photoelectric absorption and fluorescence re-emission, i.e., the custom Monte Carlo simulation tool was modified to include the effects of material fluorescence. Not included in the detector model were the effects of electron transport, conversion from X-ray energy absorbed to visible light, and the spatial migration of the visible light. The calculated detector-response curve is somewhat lower than the photoelectric absorption curve would indicate. Scattered X-ray photons can further contribute to the absorption process, which increases the calculated detector response. However, a significant fraction of the photoelectrically absorbed X-ray photons fluoresce. A significant fraction of the fluoresced photons are reabsorbed within the detector material, but some escape through the entrance and exit surfaces. Also included in the detector response model is the photon angle of incidence dependence. The above-described curve was calculated for a normally incident beam of photons. Within the custom Monte Carlo simulation tool, the photon angle of incidence is used to calculate an effective detector response value for the particular photon energy based on the increased path length through the detector material.

3.7 Calibration Model

In real-world systems, the spectrum (shape and intensity) varies with emission field angle, tube current, and voltage. Typically the detector response varies from pixel to pixel. Unless an independently calibrated detector is used to calibrate the source, an air-image calibration method embodies all of the above-stated effects. A two-point calibration procedure typically includes correcting the signal output for each detector pixel by taking a dark image to determine the zero signal input response and an air image captured with the source operated at the recommended current to determine the signal response for maximum input. The final calibration image is generated by subtracting the dark image from the air image. Calibrated images are obtained by processing the raw captured images, i.e., subtracting the dark image, dividing by the dark corrected air image, and multiplying by a code value maximum $I_o$. Ideally, processed image regions with no object obstruction should yield a value of $I_o$. In practice, the maximum code value $I_o$ is exceeded due to scatter from the object that was not accounted for in the air-image calibration procedure.

The custom Monte Carlo simulation tool employs a calibration procedure that parallels the above-described processing. Real-world sources of variation, such as detector pixel-to-pixel response variation, source tube voltage variation, and detector modulation transfer function (MTF) effects are not modeled. However, the effects of scatter from the air and source spectrum variation with emission field angle are modeled. This is achieved by modeling an air volume in the simulator and generating calibration air images unique to the different modeling scenarios.

3.8 Comparison Images and Plots

In the following analytical studies, difference images were generated by the following procedure. For a given system configuration, e.g., anode voltage, grid or no grid, etc., a Monte Carlo simulation was calculated for one projection angle of the CBCT system, and the primary (directly transmitted) and scatter (generated from the object and air) images were recorded. For the primary and scatter images, a corresponding difference image D(x,y) was calculated using (11)

$$D(x, y) = \frac{100(B(x, y) - A(x, y))}{B(x, y)},\quad(11)$$

where the signal A(x,y) represents the signal modeled with a constant spectrum, and B(x,y) represents the signal modeled with an angle-dependent spectra. For each study, the constant spectrum was sampled from a point halfway from the center pixel to the corner pixel. The emerging spectrum from the filtration was calculated using the thickness of each filter material traversed for that unique emission field angle. The graphs shown below depict horizontal traces across the difference images. The knee images were sampled through the densest part of the bone region. The head images were sampled approximately in the center.

In the following section, different modeling scenarios are presented, i.e., with and without angle-dependent spectra modeling. Each modeling scenario requires its own air-image processing. As a consequence of the modeling approach, the two different scenarios will match exactly only for an air-volume as the input object. The results for voxel-based digital phantom objects will, in general, not match when comparing calibrated images from the two different modeling scenarios. This is true even for the pixel of a symmetric system corresponding to the sampled constant spectrum. This is principally due to the calibration processing and secondarily to the normalization of the photon statistics employed within the Monte Carlo simulation tool. Therefore, the comparisons presented below should be considered as difference images, i.e., the values in the graphs represent the percentage difference in the predicted signals as a comparison between the angle-dependent modeling approach and the constant-spectrum approach.

4 Results

Figure 3:
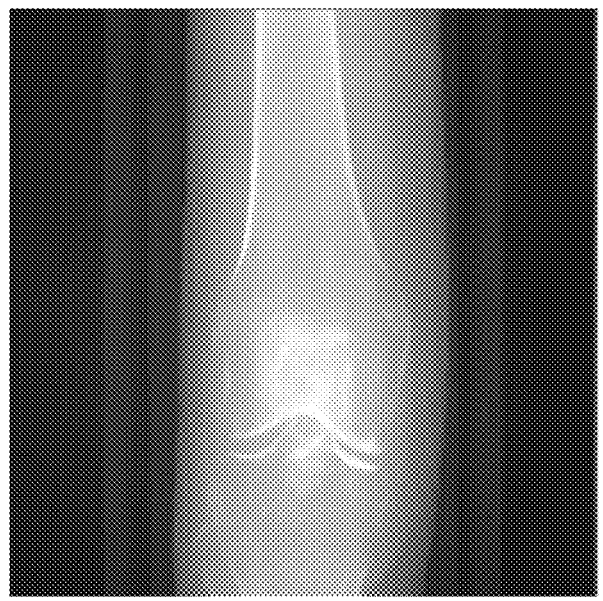
FIG. 3 is a diagram that shows a simulated primary image of a knee phantom for an orthopedic CBCT system. The rendered image was calculated as the logarithm of the primary (direct ray) signal intensity.
Figure 4:
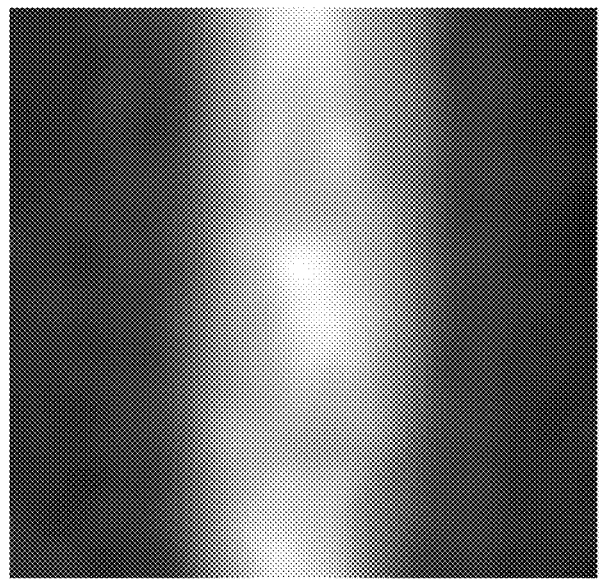
FIG. 4 is a diagram that shows a calibrated primary difference image for the knee phantom. The anode voltage was 70 Kvp, and the filtration was simple. Black corresponds to a modeling difference of −0.3% and white corresponds to a difference of 5.9%. This image is representative of the spatial pattern of the difference signals. The error in using the constant spectrum approximation is greatest behind the densest part of the object.
Figure 5:
FIG. 5 is a diagram that shows simulated primary image of the head phantom. The rendered image was calculated as the logarithm of the signal intensity. The digital phantom was edited to remove metal artifacts and synthetically extended below to simulate the extended neck region.
Figure 6:
FIG. 6 is a diagram that shows a calibrated primary signal difference image for the head phantom for an anode voltage of 90 Kvp and with simple filtration. The difference image was rendered in the linear code value domain with black corresponding to a −0.7% difference value and white corresponding to a difference value of 8.6%. The largest magnitude differences are experienced behind dense bone material.
Figure 7:
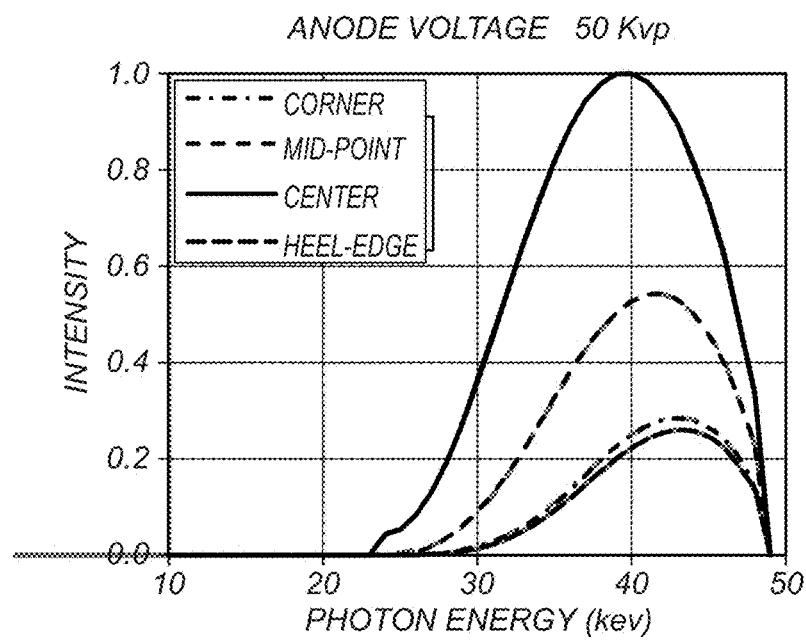
FIG. 7 is a diagram that shows a spectrum for different emission field angles for an orthopedic CBCT system with 50 Kvp anode voltage and bow-tie filter.
Figure 8:
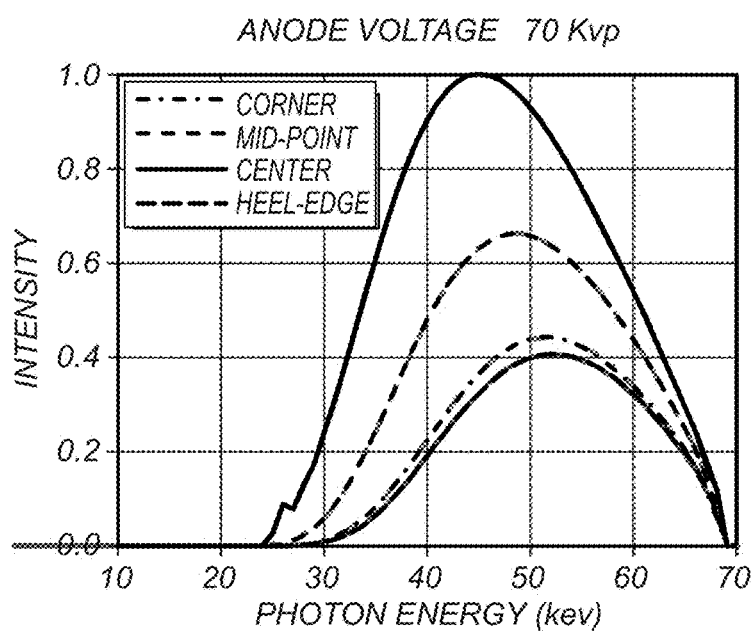
FIG. 8 is a diagram that shows a spectrum for different emission field angles for an orthopedic CBCT system with 70 Kvp anode voltage and bow-tie filter.
Figure 9:
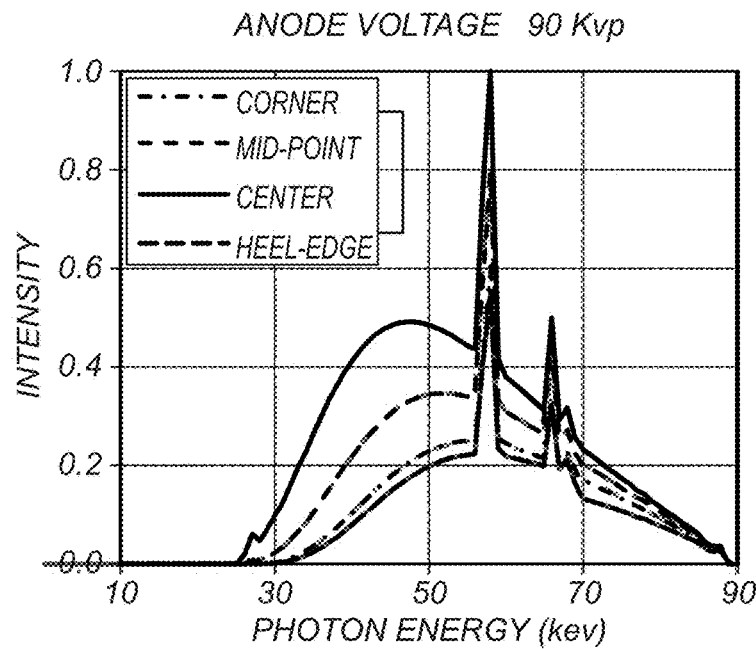
FIG. 9 is a diagram that shows a spectrum for different emission field angles for an orthopedic CBCT system with 90 Kvp anode voltage and bow-tie filter.
Figure 10:
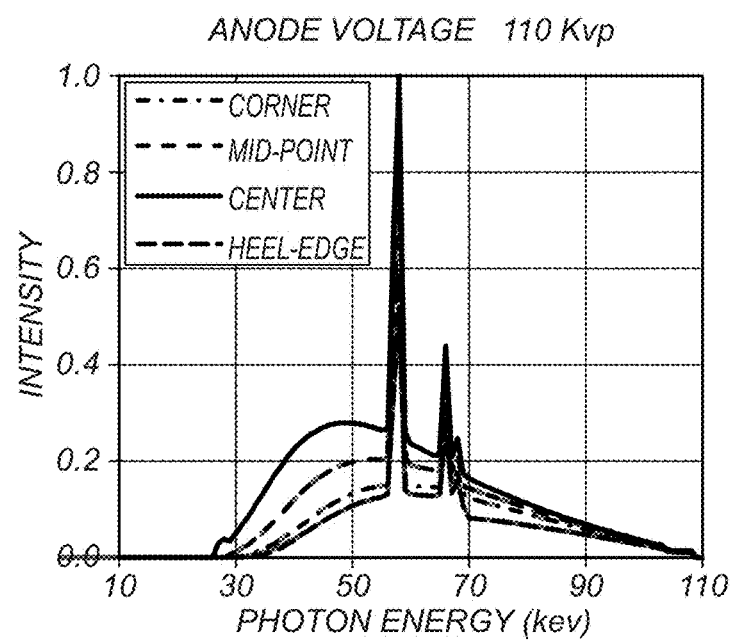
FIG. 10 is a diagram that shows a spectrum for different emission field angles for an orthopedic CBCT system with 110 Kvp anode voltage and bow-tie filter.

For each of the analytical examples described below, Monte Carlo simulations of projection images were performed using either the knee or head digital phantom. The custom Monte Carlo simulation tool allows the individual imaging signals to be recorded separately. Therefore, for each imaging scenario, i.e., system, phantom, and anode voltage, filtration, etc., the primary and scatter imaging photons were recorded to produce a primary image and scatter image, respectively. FIG. 3 shows the primary image of the knee phantom as modeled through the exemplary orthopedic CBCT system. FIG. 5 depicts the primary image for the head phantom. Both primary images were rendered in the logarithmic code value domain in a similar fashion as projection radiographs are presented. Thus, white regions in the images represent highly attenuated pathways. The dark portions of FIGS. 3 and 4 represent no attenuation by the object, i.e., air-image regions. FIG. 4 depicts a calibrated primary difference image for the knee phantom for an anode voltage of 110 Kvp. The difference image is rendered in the linear code-value domain. White regions relate to more positive difference values (white relates to a 7.5% difference value). Black regions relate to more negative difference values with black corresponding to a difference value of −2.4%. FIG. 6 depicts a calibrated primary difference for the head phantom for an anode voltage of 90 Kvp. For this image, the range of difference values is from −0.7% to +8.6%. Images 1b and 2b are representative of the spatial activity in the difference images used for analysis.

4.1 Computational Performance

The Monte Carlo simulation tool was exercised with and without the emission field angle-dependent spectra feature to determine the computational burden. The average percentage increase in the CPU time for the knee phantom simulations was 7.5, 9.9, 13.0, and 15.6% for the scenarios corresponding to anode voltages of 50, 70, 90, and 110 Kvp, respectively. The average percentage increase in the CPU time for the head phantom simulations was 28.8, 28.3, 30.2, and 30.7% for the scenarios corresponding to anode voltages of 50, 70, 90, and 110 Kvp, respectively. While these reported increases are based on the entire photon simulation time, the actual time required to generate the angle-dependent spectral emission was only 6.2%. The additional increase beyond 6.2% is due to the change in the photon energies traced through the object. The head phantom is more radio opaque than the knee phantom, requiring 15% longer run times for the $10^9$ photons used for the simulations.

The mean spectral energy for the orthopedic CBCT system with the bow-tie filter was 37.9, 46.8, 54.5, and 60.5 key for the anode voltage scenarios of 50, 70, 90, 110 Kvp, respectively. The corresponding rejection strategy efficiency (percent of accepted photons) was 56.9, 68.0, 73.7, and 76.6% for the voltage scenarios of 50, 70, 90, 110 Kvp, respectively. For the scenarios with simple filtration, the mean spectral energy was 37.9, 46.6, 54.2, and 60.1 key voltage for scenarios of 50, 70, 90, 110 Kvp, respectively.

4.2 Emission Field-Angle Spectra

The spectrum for different emission field angles is shown in the FIGS. 7, 8, 9, and 10 for the exemplary orthopedic CBCT system with bow-tie filtration for the anode voltage scenarios of 50, 70, 90, and 110 Kvp, respectively. For each of these graphs, the spectrum of photon emission is shown for four points on the detector: center pixel, mid-point pixel (halfway between the center and corner pixel), corner pixel, and a heel-edge pixel located on the anode side of the detector centered vertically. The most dramatic aspect of the spectral plots is the overall intensity change with emission field angle. The next most prominent aspect is the spectrum hardening caused by the increased copper thickness of the bow-tie filter as the emission field angle changes from center to corner. The X-ray beam is hardest in the anode heel region due to the increase in anode material thickness required for the escaping X-ray photons.

4.3 Example 1

Knee Phantom with Simple Filtration

Figure 11:
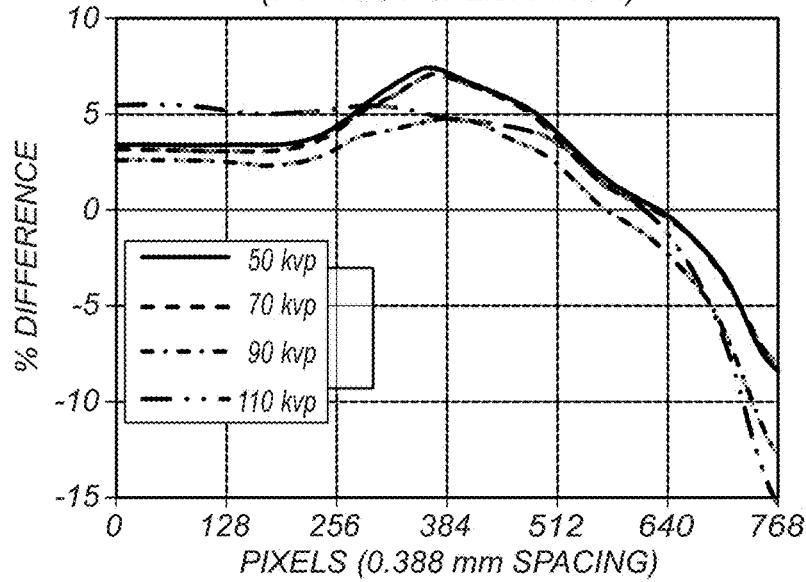
FIG. 11 is a diagram that shows uncalibrated primary image traces for the knee phantom with a simple filtration modeled. Without calibration applied, the right side of graph shows large magnitude differences due to the anode heel effect.
Figure 12:
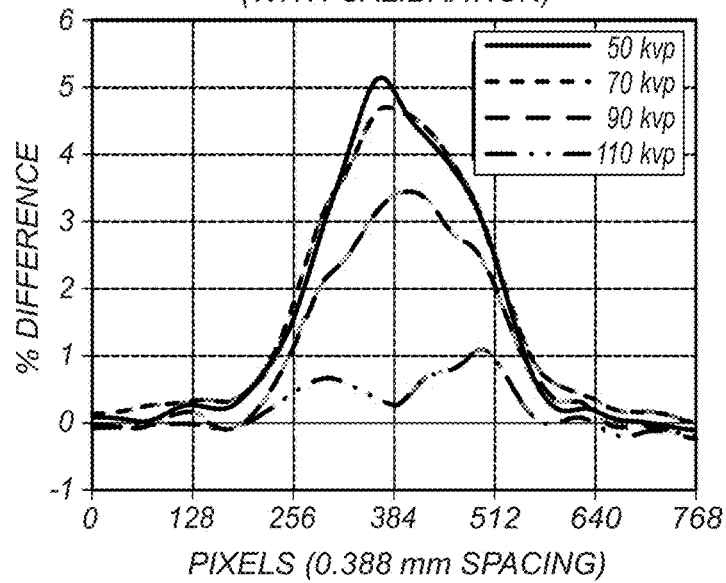
FIG. 12 is a diagram that shows calibrated primary image traces for the knee phantom with a simple filtration modeled. With calibration applied, the intensity falloff of the anode heel effect is largely removed.
Figure 13:
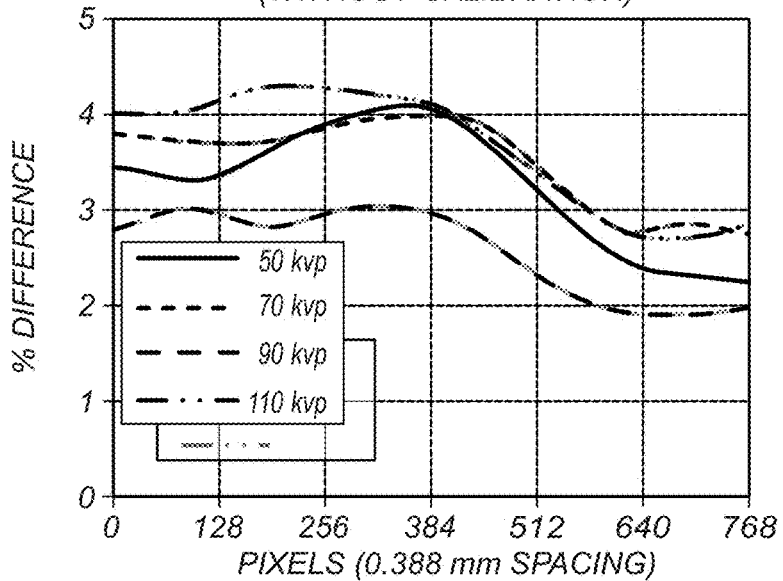
FIG. 13 is a diagram that shows knee phantom scatter image traces with no calibration applied—a simple filtration is modeled. Without calibration applied, the right side of graph shows only a modest drop in the difference signal. This is principally due to the dispersive nature of scattered radiation, i.e., each pixel receives scattered radiation from all voxels in the object.
Figure 14:
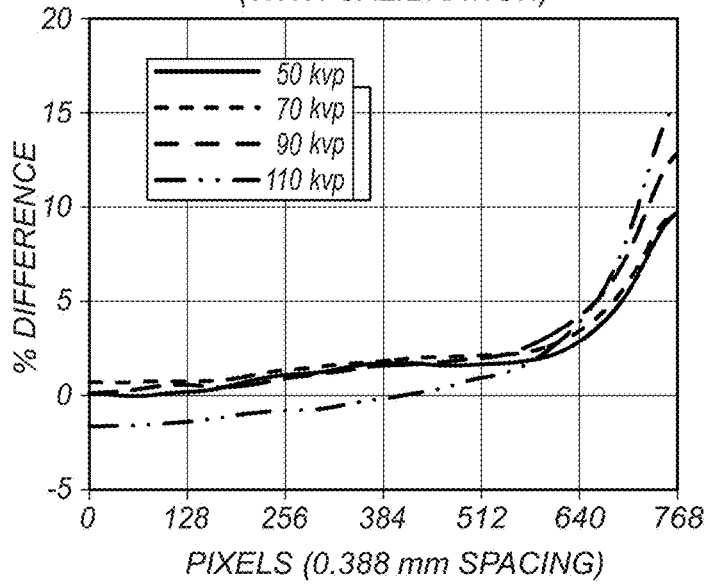
FIG. 14 is a diagram that shows knee phantom scatter image traces with calibration applied—a simple filtration is modeled. The relatively flat scatter images are amplified with the applied calibration air image producing large magnitude differences on the heel-effect side of the detector.

Example 1 is a comparison study for the exemplary orthopedic CBCT system described above. The filtration stack of filters consisted of a 2.0 mm aluminum plate (modeling the inherent filtration) with a 0.2 mm copper plate. The system was modeled with four different anode voltages: 50, 70, 90, and 110 Kvp. The difference signal plots for all anode voltage scenarios are shown in the FIGS. 11, 12, 13, and 14. For example, FIG. 11 shows the primary image difference signals with no calibration air image applied, while FIG. 12 shows curves with calibration air-image normalization. FIGS. 13 and 14 show the corresponding difference signal traces calculated for the scatter images.

The uncalibrated primary signals for the four anode voltage sub-cases show roughly the same pattern. No anode heel effect was modeled for the constant spectrum scenarios, which explains the sharp rise in the magnitude of the difference signals on the detector anode side. For the image regions away from the heel-effect zone, the error signals range from 5 to 7% with the 50 Kvp scenario showing the largest magnitude. The sensitivity-to-anode voltage is better depicted by FIG. 12, which shows the difference signals for the calibrated primary images. The differences for the two modeling approaches range from 1 to 5% for the image-central regions behind the knee. For the air regions, the difference signals are close to zero because air does not appreciably attenuate X-rays and the calibration normalization compensates for differences in the beam intensity. The slight negative difference signal values for the anode side are most likely due to imperfections in the analytical calibration image-generation process.

FIGS. 13 and 14 show the difference signal traces derived from the calculated scatter images for the uncalibrated and calibrated signals, respectively. The uncalibrated scatter images show a more even spatial pattern. This is primarily due to the fact that each detector pixel receives scattered radiation from voxels throughout the object. The difference signals do show an asymmetry due to the heel effect, with larger signal differences for lower anode voltages. The calibrated scatter signals show a marked difference on the anode side. Although the difference percentages are large, the actual scatter values of the calibrated images are a relatively small percentage of the open-air target code value $I_o$. However, when correcting measured projection images, the calibration air image must be taken into account. That is, uncalibrated/calibrated scatter images should be subtracted from uncalibrated/calibrated measured images prior to reconstruction.

4.4 Example 2

Knee Phantom with a Bow-Tie Filter

Figure 15:
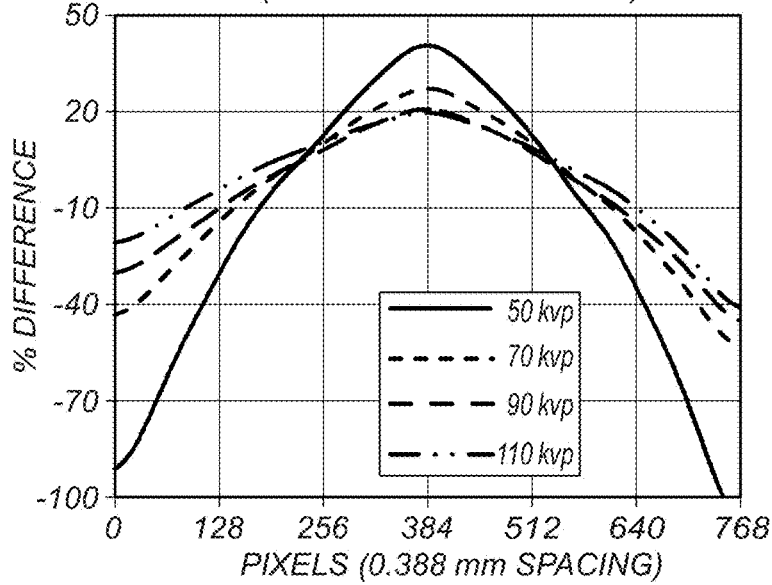
FIG. 15 is a diagram that shows knee phantom primary image traces with bow-tie filtration and no calibration applied. Large magnitude differences are evident on both sides of the image due to the attenuation of the bow-tie filter. The intensity effect on the heel side is even greater.

Example 2 is a comparison study for the exemplary orthopedic CBCT system, as described in Example, 1 with the addition of a bow-tie filter. Overall, the magnitude of the difference signals with the addition of the bow-tie filter is considerably higher than for the study with simple filtration (Example 1). The uncalibrated primary image difference signals, shown in FIG. 15, exhibit large magnitudes at the edges of the images. This is principally due to the spatial pattern of the bow-tie filter attenuation (see FIG. 2). (The modeled copper thickness is approximately 0.6 mm at the edge and 0.12 mm at the center.) The applied calibration can reduce or minimize the differences in the edge regions (air regions). For the regions behind the knee, the calculated primary image values are lower when using the angle-dependent spectra modeling approach. The magnitude of the differences is roughly twice as great as for the scenario of simple filtration, i.e., −4% to −7% vs. +1 to +5% for Example 1 with simple filtration behind the dense part of the knee. The effect is greatest for lower anode voltage scenarios. The calibrated scatter signal differences are +6% directly behind the knee for the bow-tie scenario vs. 0 to 2% for the simple filtration scenario.

4.5 Example 3

Knee Phantom with Anti-Scatter Grid

The exemplary orthopedic CBCT system is usually operated with an anti-scatter grid. Example 3 is a study of the system modeled with the simple filtration of example 1 with the addition of an anti-scatter grid. The corresponding graphs are not shown since the curves are very similar to the graphs for the scenario without a grid. The magnitude of the primary difference signals is within approximately 1% of the curves shown for example 1 exhibiting slightly less sensitivity to the anode voltage. However, the magnitude of the scatter difference signals was slightly larger by approximately 1 to 1.5%. In effect, the anti-scatter grid behaves like a parallel plate filter of the matrix material (aluminum) placed between the detector and the object. Although the anti-scatter grid contains lead absorber plates, these are oriented essentially parallel to the incoming primary X-ray photons and contribute very little to the system's photon energy sensitivity.

4.6 Example 4

Head Phantom with Simple Filtration

Figure 19:
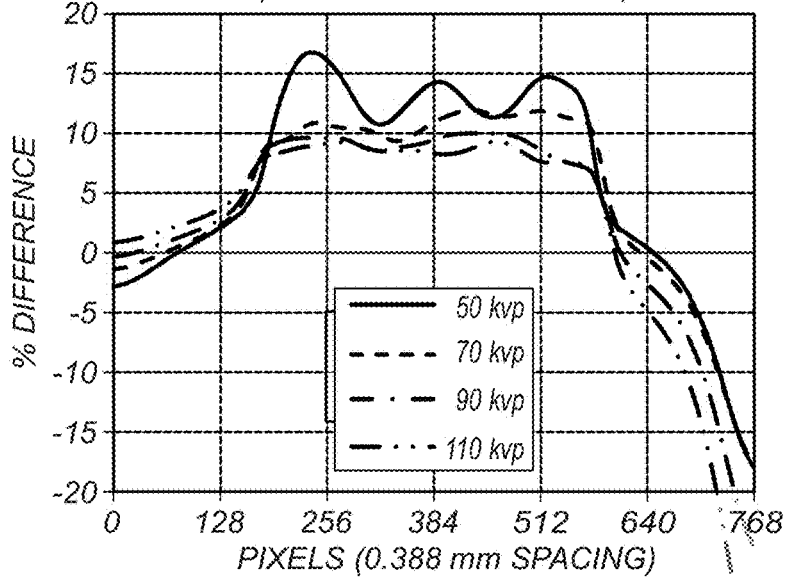
FIG. 19 is a diagram that shows uncalibrated primary image difference signals for the digital head phantom with a simple filtration modeled. The magnitude of the difference signals is significantly higher than for the knee phantom due to the overall higher material attenuation.
Figure 20:
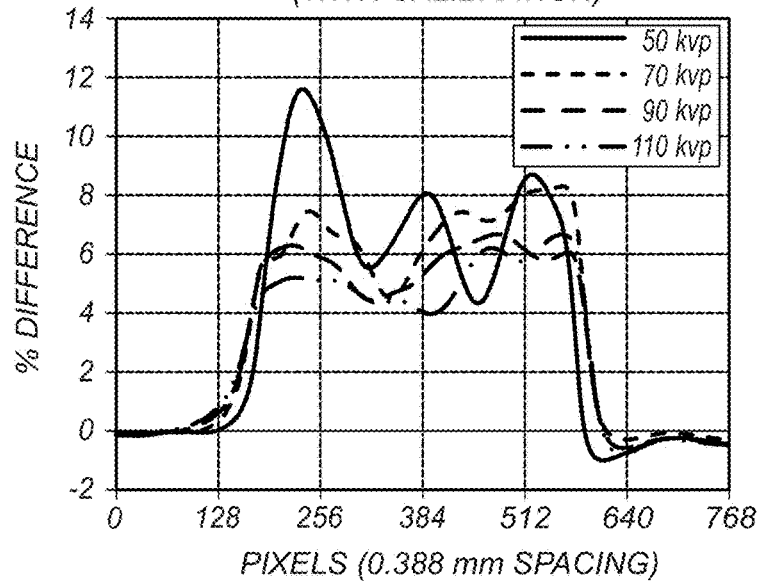
FIG. 20 is a diagram that shows calibrated primary image difference signals for the digital head phantom with a simple filtration modeled. The calibration normalization reduces the heel-effect intensity anomaly for the primary signals.
Figure 21:
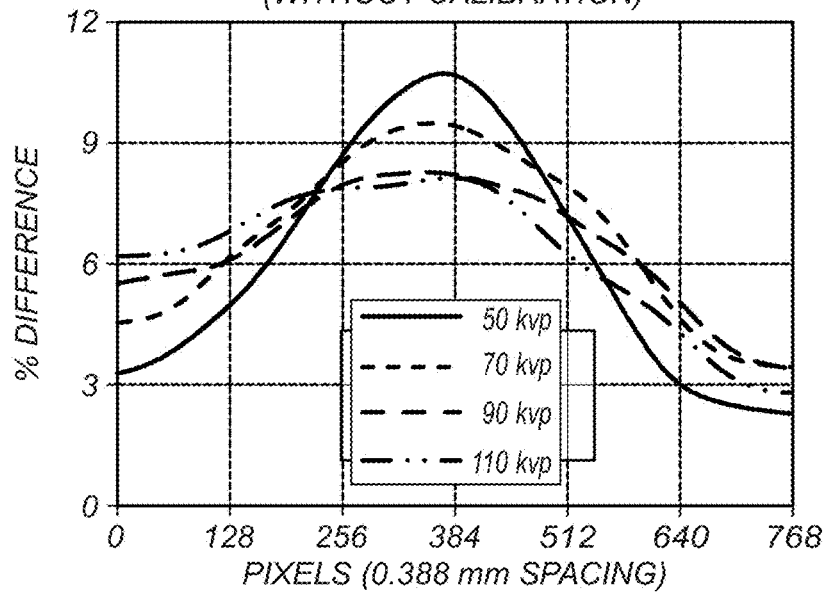
FIG. 21 is a diagram that shows uncalibrated scatter image difference signals for the digital head phantom with a simple filtration modeled. The magnitude differences are much greater than for the case of the knee phantom. The heel effect intensity falloff produces an asymmetry in the scatter image difference signals.
Figure 22:
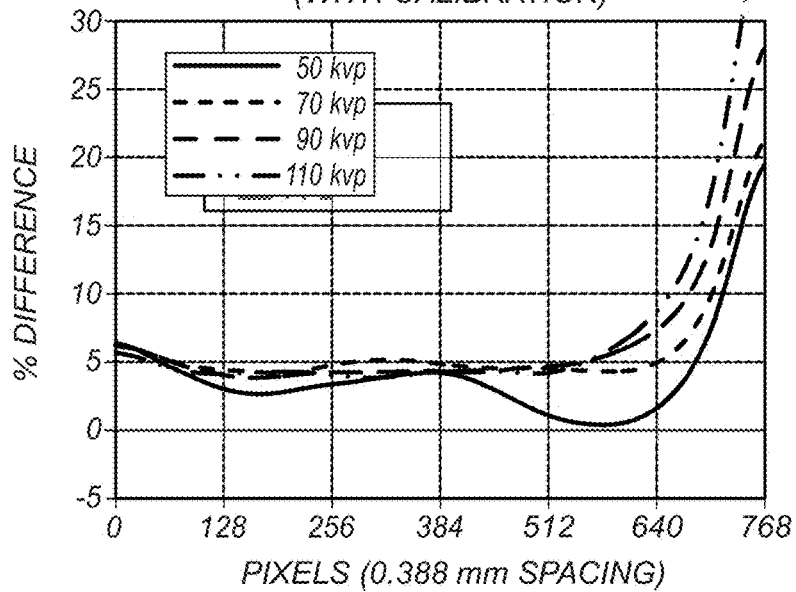
FIG. 22 is a diagram that shows calibrated scatter image difference signals for the digital head phantom with a simple filtration modeled. The calibration normalization amplifies the difference signals for the image regions behind the anode heel zone.

Example 4 is a study of the digital head phantom with simple filtration modeled. The primary difference signals are shown for uncalibrated and calibrated scenarios in FIGS. 19 and 20, respectively, and scatter difference signals for uncalibrated and calibrated scenarios in FIGS. 21 and 22, respectively. The magnitude of the uncalibrated primary image difference signals is generally much higher for the head phantom—approximately 8 to 15% vs. 5 to 7% for the head and knee scenarios, respectively, for the same simple filtration. The calibrated primary image difference signals is also much higher—4 to 11% behind the head vs. 1 to 5% behind the knee. The uncalibrated scatter difference signals range from 8 to 10% directly behind the head vs. 3 to 4% directly behind the knee. The calibrated scatter difference signals range from 4 to 5% behind the head and approximately 0 to 2% behind the knee. The greater magnitude of the difference signals is most likely due to the greater attenuation of the head phantom. Given identical filtration, higher attenuating objects will show larger spectral effects. Hence, the constant-spectrum approximation is more appropriate for less dense objects.

4.7 Example 5

Head Phantom with a Bow-Tie Filter

Figure 23:
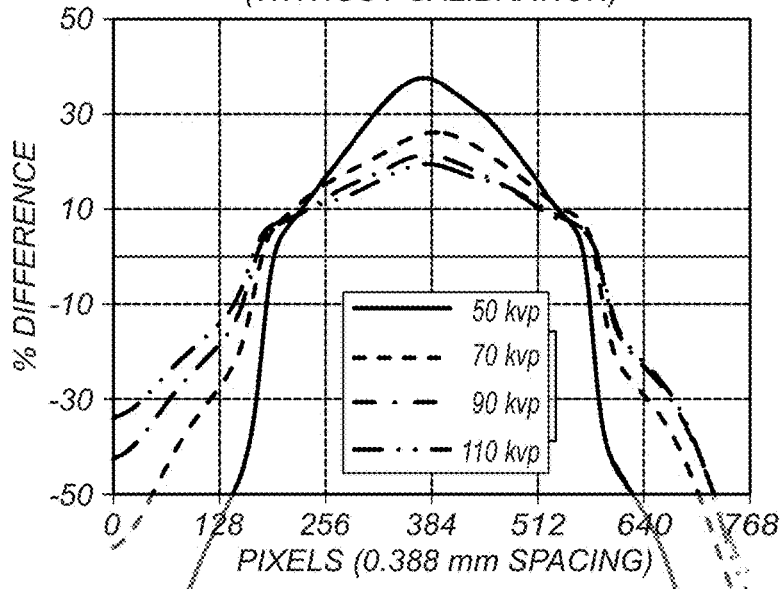
FIG. 23 is a diagram that shows head phantom primary image difference signals with bow-tie filtration and no calibration applied. The large magnitude differences at the edges of the images are a result of the bow-tie induced increased attenuation with emission field angle.
Figure 24:
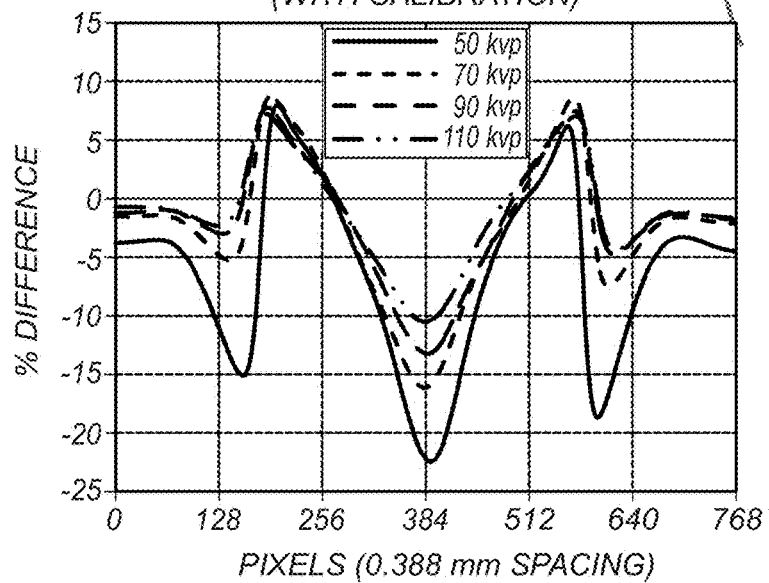
FIG. 24 is a diagram that shows head phantom primary image difference signals with bow-tie filtration and calibration applied. The application of the calibration normalization reduced the large magnitude differences at the image edges. The difference is reduced to near zero at the edges of the image corresponding to air-image region.
Figure 25:
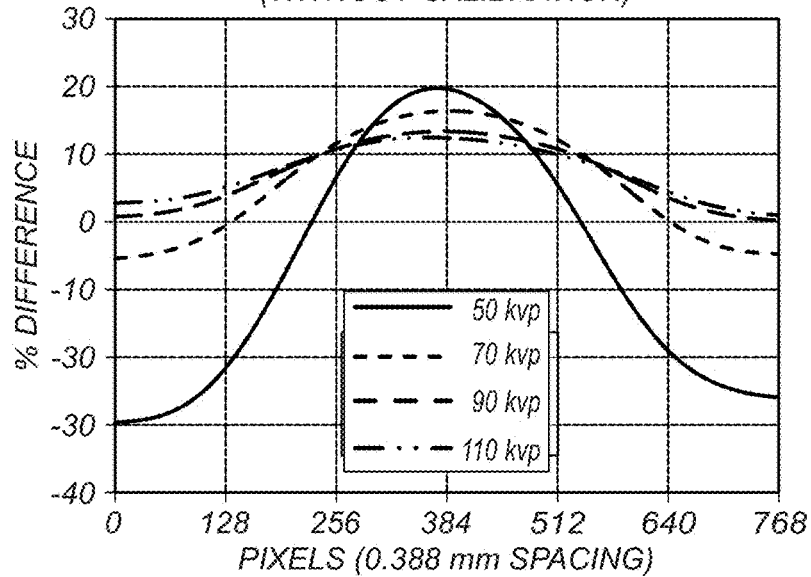
FIG. 25 is a diagram that shows head phantom scatter image traces with no calibration applied for an orthopedic CBCT system, with bow-tie filtration added. The scatter difference signals are largest behind the densest part of the head phantom. The magnitude of the difference signals is only slightly higher than for the case of simple filtration.
Figure 26:
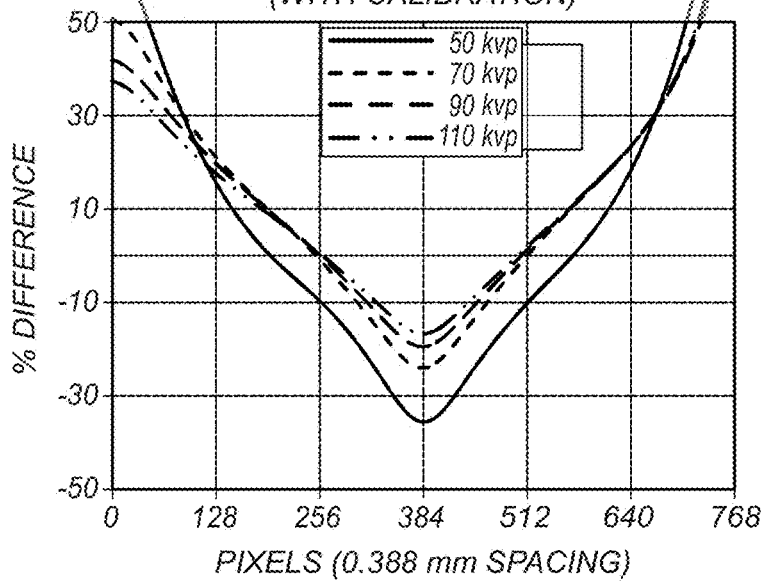
FIG. 26 is a diagram that shows head phantom scatter image difference signals with calibration applied for an orthopedic CBCT system, with bow-tie filtration added. With calibration normalization applied, the scatter difference signals are inverted relative to the uncalibrated signals. Part of the central depression in the curves is caused by the mismatch in smoothing between the calibration image and the image signals.

The same CBCT system modeled in Example 4 is modeled in Example 5 with the bow-tie filter substituted for the flat plate of copper. FIGS. 23 and 24 depict the uncalibrated and calibrated primary image difference signals, respectively. FIGS. 25 and 26 depict the uncalibrated and calibrated scatter signals, respectively. Compared to the results from Example 4 (modeling simple filtration), the inclusion of the bow tie amplifies the difference signals. The uncalibrated primary signal differences range from +10 to +40% behind the head vs. +8 to +15% for the simple filtration of Example 4. Similarly, the calibrated primary signal differences show much wider range −30 to +20% vs. +4 to +11%. The uncalibrated scatter difference signals range from +10 to +20% directly behind the head for the bow-tie scenario vs. +8 to +10% for the simple filtration scenario. Similarly, the calibrated scatter signal differences range from −14 to −38% directly behind the head vs. +4 to +5% for the same region for the simple filtration scenario.

Figure 16:
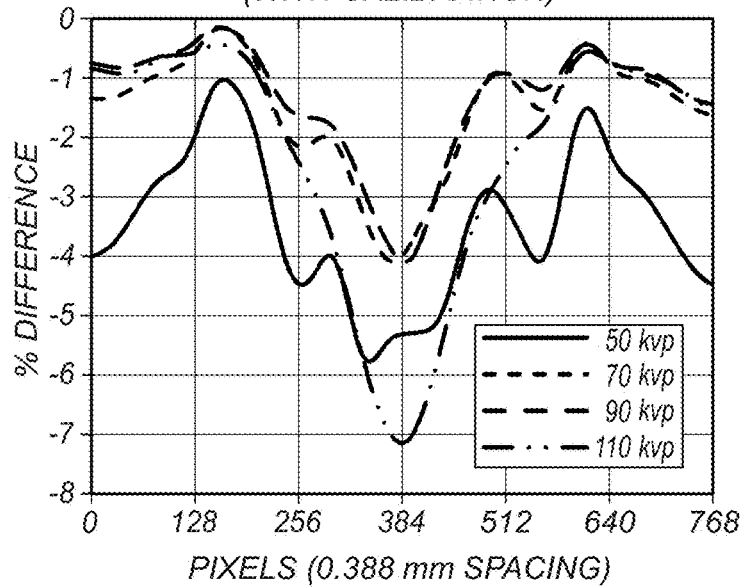
FIG. 16 is a diagram that shows knee phantom primary image traces with bow-tie filtration and calibration applied. The intensity effects toward the image edges are mostly eliminated for air regions. The regions behind the knee show significantly higher magnitude differences due to the bow-tie filter. Part of the central depression in the curves is caused by the mismatch in smoothing between the calibration image and the image signals.
Figure 17:
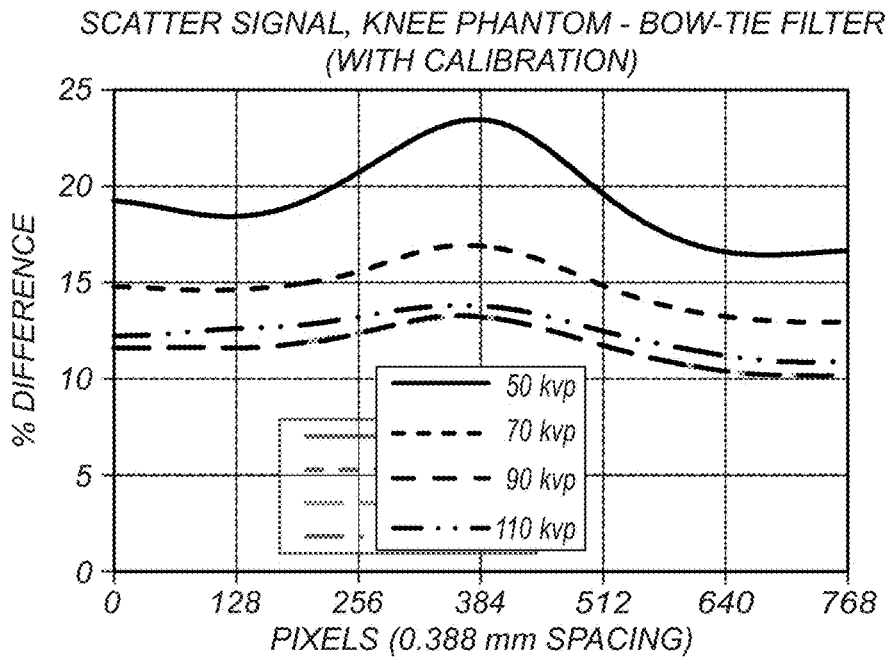
FIG. 17 is a diagram that shows scatter image traces with no calibration applied for an orthopedic CBCT system, with bow-tie filtration added. Without calibration applied, the difference signal patterns are relatively constant across the images. The traces show that higher magnitude differences are experienced for lower anode voltage scenarios.
Figure 18:
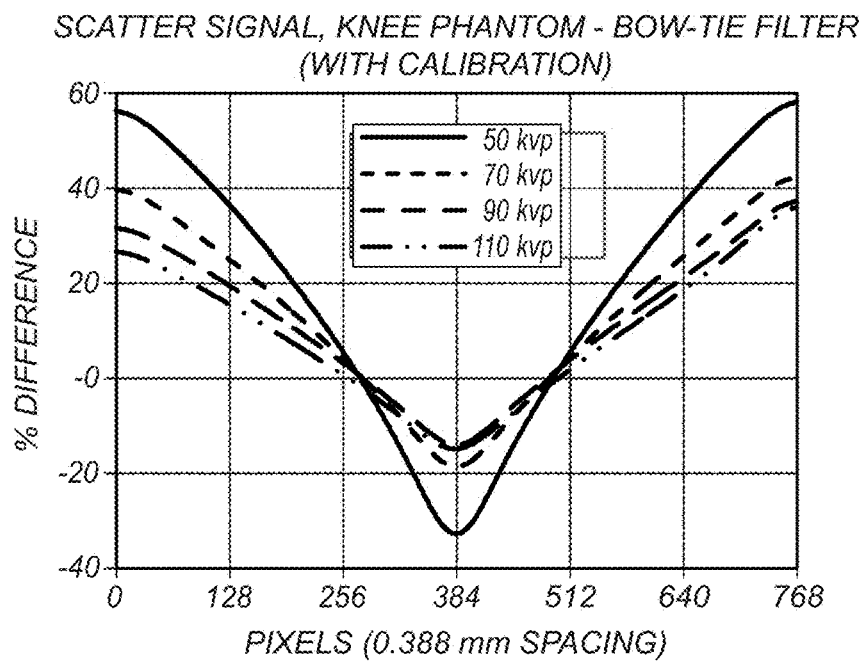
FIG. 18 is a diagram that shows scatter image traces with calibration applied for an orthopedic CBCT system, with bow-tie filtration added. The relatively flat scatter images are amplified with the applied calibration air image, producing large magnitude differences on both sides of the detector. Part of the central depression in the curves is caused by the mismatch in smoothing between the calibration image and the image signals.

The large increase in magnitude of the uncalibrated primary image difference signals is a direct result of the greater bow-tie attenuation toward the edges of the image. This effect is pronounced for the 50 Kvp anode scenario. The calibrated results show the difference signals approaching zero for the air-image regions at the edges of the image. The strong negative difference signal values directly behind the knee (shown in FIG. 16) is also evident behind the center of the head (shown in FIG. 24). The uncalibrated scatter difference signals show a greater range of variation, −22% to +12% (shown in FIG. 25) for the head bow-tie scenario vs. 0 to 14% (shown in FIG. 21) for the head-simple filtration scenario. Neglecting the anode heel-effect zone, the calibrated scatter difference signals for the bow-tie filtration scenario show a large magnitude range of +25% to −25% (shown in FIG. 26) vs. only +6 to +12% range for the simple filtration scenario (shown in FIG. 22).

TABLE 1

|  | Phantom, filtration | Primary (uncalibrated) | Primary (calibrated) | Scatter (uncalibrated) | Scatter (calibrated) |
| --- | --- | --- | --- | --- | --- |
| Example 1 | knee, simple | +4.7% to +7.1% | +0.3% to +4.9% | +3.0% to +4.1% | −0.2% to +1.8% |
| Example 2 | knee, bow tie | +20.0% to +40.0% | −4.0% to −7.1% | +13.2% to +23.5% | −14.0% to −32.7% |
| Example 3 | knee, grid | +4.4% to +6.4% | +2.3% to +3.1% | +4.0% to +5.4% | +1.9% to +2.4% |
| Example 4 | head, simple | +8.3% to +14.2% | +4.1% to +8.0% | +8.1% to +10.7% | +4.2% to +4.9% |
| Example 5 | head bow tie | +10.0% to +37.0% | −10.5% to −22.0% | +12.4% to +19.6% | −16.7% to −35.6% |

The signal difference ranges in the center of the traces for the FIGS. 2, 3, 4, 5, and 6, described by imaging Examples 1, 2, 3, 4, and 5, are shown in Table 1. The numbers in Table 1 encapsulates the overall trends in the data. The simple filtration scenarios (Examples 1 and 4) have lower magnitude differences than their bow-tie counterparts (Examples 2 and 5). The numbers for the grid scenario (Example 3) are slightly larger than the scenario without grid (Example 1).

5. Results

Monte Carlo simulation implementations, as well as most reconstruction algorithms described in the literature, model the system with an angle-independent, constant-spectrum approximation. Often the spectrum corresponding to the central ray is chosen as a representative spectrum. This is typically also the softest X-ray spectrum. What is the expected prediction error for primary and scatter images in this approximation?

In general, emission field angle-dependent spectra modeling is most important for systems that: (a) have large emission field angles, (b) image dense objects, (c) employ field-varying thickness filters, or (d) exhibit pronounced anode heel effects. In practice, severe heel-effect intensity problems can be mitigated by tilting the anode, thus operating the anode at a greater angle. The above simulations were conducted with the simulated anode tilted at 2°.

For systems employing minimal additional spectrum-shaping, flat-plate filters, the prediction errors should be relatively small. The maximum prediction differences for the knee phantom with the exemplary orthopedic CBCT system were approximately 3% and 5% for the primary and scatter images, respectively (neglecting the heel-effect zone). The largest emission field angle for the exemplary orthopedic system is approximately 20.6°. Systems exhibiting smaller emission field angles should incur even smaller prediction errors.

The predictions errors for systems employing anti-scatter grids should be slightly higher. From a emission field-angle-dependent modeling perspective, anti-scatter grids produce similar effects to source filters. The prediction difference magnitudes for the primary signals were approximately the same when an anti-scatter grid was included in the model. The calibrated scatter difference signals were approximately 2.4% with the grid vs. 1.8% without the grid.

The denser objects produce greater differences between the constant spectrum approximation and field angle-dependent modeling approaches. Therefore, larger prediction errors for both primary and scatter signals should be expected when modeling the source with a constant spectrum. This is true even for the case of simple filtration. The magnitude of the calibrated primary difference signals were approximately 12% for the head and 3% for the knee. The magnitude of the uncalibrated scatter difference signals were approximately 12% for the head and 5.5% for the knee.

Emission field angle-varying filtration, such as a bow-tie filter, produce significantly varying emission field angle-dependent spectra (see FIGS. 7, 8, 9, and 10). The modeling prediction differences were significantly larger with the bow-tie filter for the knee phantom. The knee phantom calibrated primary difference signal magnitudes measured approximately 8% with the bow-tie filter vs. 3% with simple filtration and 15% vs. 5.5% for the uncalibrated scatter signals, respectively.

The modeling differences between the two approaches for the head phantom, with and without the bow-tie filter, showed a similar sensitivity. The range of difference signal experienced was approximately +4.1 to +8.0% for the simple filters vs. a range of −10.5 to −22% for the bow-tie filter. Similarly, the calibrated scatter difference signals ranged from +4.2 to +4.9% behind the head for the simple filtration vs. From −16.7 to −35.6% for the bow-tie filter scenario.

Monte Carlo simulation tools designed for analyzing X-ray capture systems model the source X-ray emission by a constant spectrum even though it is widely understood that the spectrum varies with emission field angle. Presented here are exemplary embodiments of apparatus, methods and/or algorithms that can model the X-ray emission as emanating within the anode material at a fixed depth and traversing through a stack of filtration materials corresponding to the system geometry. Exemplary embodiments can use probabilistic rejection scheme approaches to generate random X-ray photons that conform to the expected spectrum as a function of field angle. As with most analytical modeling methods, there is a tradeoff between accuracy and speed of computation. Monte Carlo exemplary embodiments using the varying spectrum feature required approximately 6% greater computational resources when compared to modeling the system by a constant spectrum. However, the total additional computational time for simulations employing a bow-tie filter model took considerably longer: 13% and 30% for the head and knee phantoms, respectively. This is primarily due to the spectral shift toward higher photon energies.

All modeling constructs are approximations, and as such, have limitations. The canonical approximation of the constant spectrum was compared with the presented varying spectrum model for an exemplary CBCT system for anode voltages ranging from 50 to 110 Kvp. For X-ray capture systems that employ simple flat-plate filters of minimal thickness, the constant spectrum approximation works reasonably well. For these imaging scenarios, the calculated differences for the primary and scatter signals for the knee phantom were approximately 5% and 3%. Denser objects amplify the difference between the modeling approaches even for the case of simple filtration. For the much denser head phantom, the calculated differences were 15% and 11% for the primary and scatter signals, respectively. Anti-scatter grids produce similar effects to source filters made of the same material. The calculated signal differences were roughly twice as large for the knee phantom imaged with simple filtration and an anti-scatter grid. Bow-tie filters are designed specifically to reduce X-ray beam intensities for greater emission field angles. The largest calculated signal differences were for the imaging scenarios including a bow-tie filter. Within a single image, the primary and scatter signal differences calculated for the head phantom ranged from −6% to +13% and −25% to +25%, respectively.

Another aspect of this application is to provide methods and/or systems capable of increased quality (e.g., MTF, resolution, contrast) in resultant volume DR image reconstruction such as CBCT volume DR image reconstruction. CBCT imaging apparatus and imaging algorithms used to obtain 3-D volume images using such systems are well known in the diagnostic imaging art and are, therefore, not described in detail in this application. CBCT imaging apparatus, imaging algorithms and/or methods can be used to generate 3D volume data used in certain exemplary embodiments according to this application.

In typical applications, a computer or other type of dedicated logic processor for obtaining, processing, and storing image data is part of the CBCT system, along with one or more displays for viewing image results. A computer-accessible memory is also provided, which may be a non-volatile memory storage device used for longer term storage, such as a device using magnetic, optical, or other data storage media. In addition, the computer-accessible memory can comprise an electronic memory such as a random access memory (RAM) that is used as volatile memory for shorter term data storage, such as memory used as a workspace for operating upon data or used in conjunction with a display device for temporarily storing image content as a display buffer, or memory that is employed to store a computer program having instructions for controlling one or more computers to practice method and/or system embodiments according to the present application.

Figure 27:
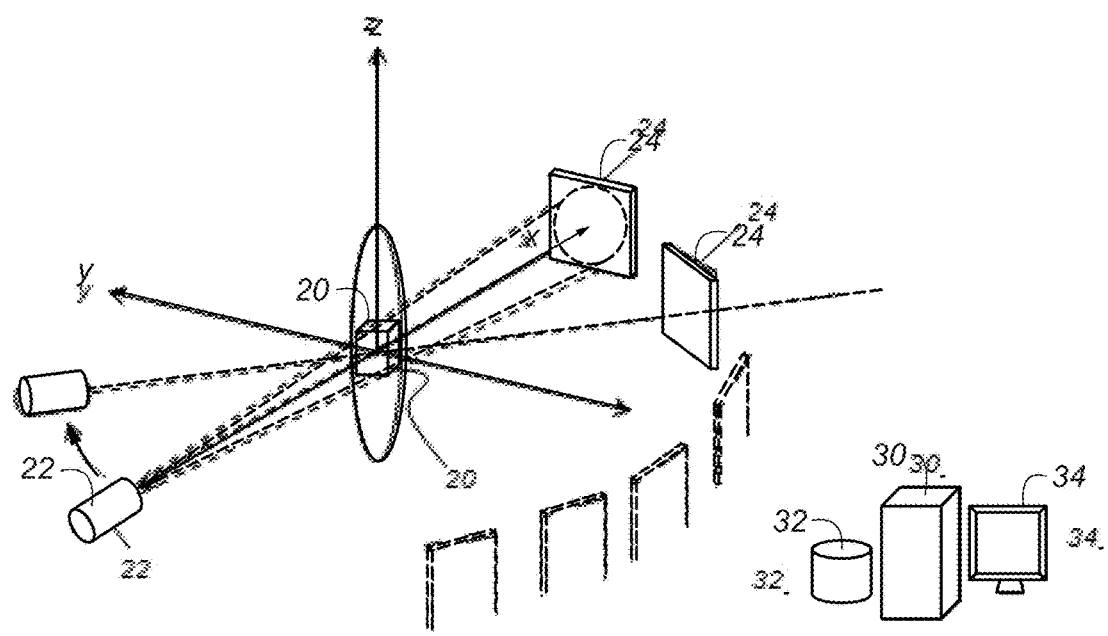
FIG. 27 is a schematic diagram showing components and architecture used for conventional CBCT scanning.

To understand exemplary methods and/or apparatus embodiments according to the present application and problems addressed by embodiments, it is instructive to review principles and terminology used for CBCT image capture and reconstruction. Referring to the perspective view of FIG. 27, there is shown, in schematic form and using exaggerated distances for clarity of description, the activity of an exemplary conventional CBCT imaging apparatus for obtaining the individual 2-D images that are used to form a 3-D volume image. A cone-beam radiation source 22 directs a cone of radiation toward a subject 20, such as a patient or other imaged subject. A sequence of images of subject 20 is obtained in rapid succession at varying angles about the subject over a range of scan angles, such as one image at each 1-degree angle increment in a 200-degree orbit. A DR detector 24 is moved to different imaging positions about subject 20 in concert with corresponding movement of radiation source 22. For example, such corresponding movement can have a prescribed 2D or 3D relationship. FIG. 27 shows a representative sampling of DR detector 24 positions to illustrate how these images are obtained relative to the position of subject 20. Once the needed 2-D projection images are captured in a prescribed sequence, a suitable imaging algorithm, such as FDK filtered back projection or other conventional technique, can be used for generating the 3-D volume image. Image acquisition and program execution are performed by a computer 30 or by a networked group of computers 30 that are in image data communication with DR detectors 24. Image processing and storage is performed using a computer-accessible memory in image data communication with DR detectors 24 such as computer-accessible memory 32. The 3-D volume image or exemplary 2-D image data can be presented on a display 34.

Figure 28:
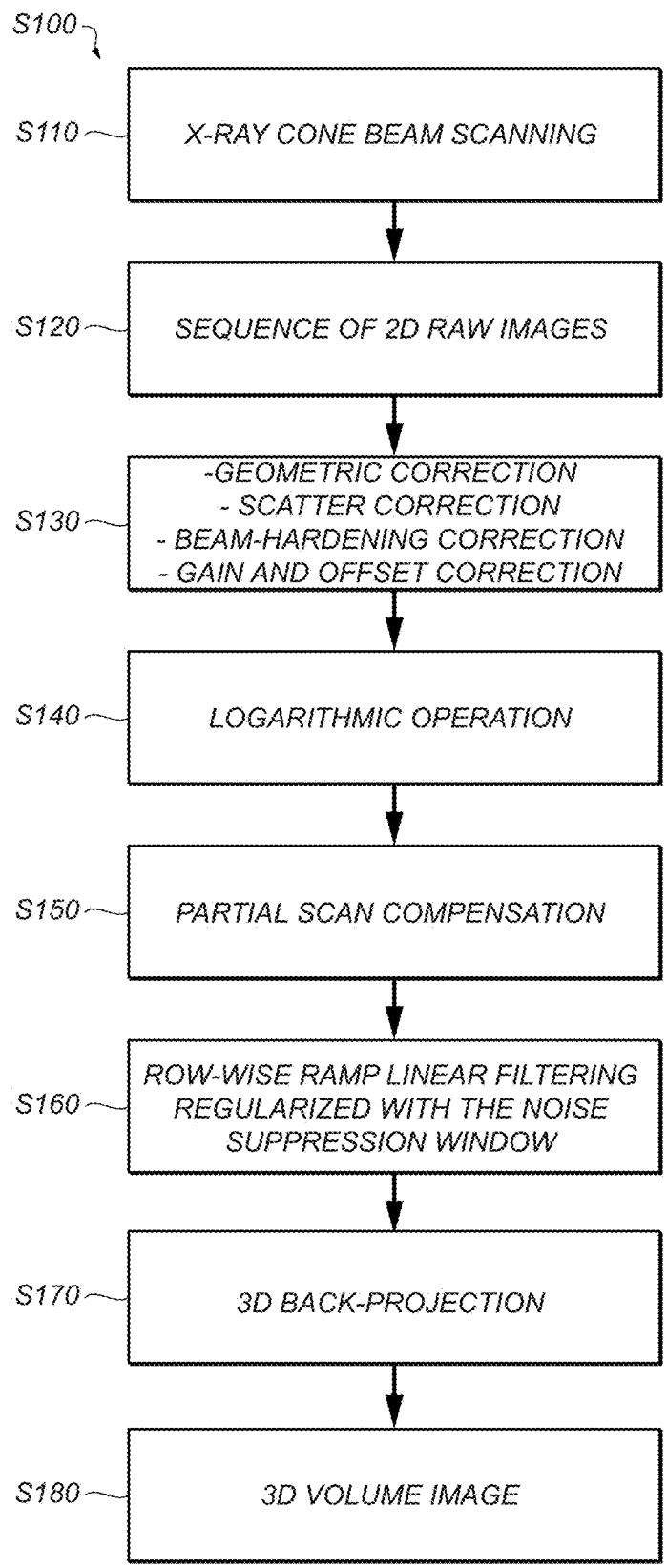
FIG. 28 is a logic flow diagram showing the sequence of processes used for conventional CBCT volume image reconstruction.

The logic flow diagram of FIG. 28 shows a conventional image processing sequence S100 for CBCT reconstruction using partial scans. A scanning step S110 directs cone beam exposure toward the subject, enabling collection of a sequence of 2-D raw data images for projection over a range of angles in an image data acquisition step S120. An image correction step S130 then performs standard processing of the projection images such as but not limited to geometric correction, scatter correction, gain and offset correction, and beam hardening correction. A logarithmic operation step S140 obtains the line integral data that is used for conventional reconstruction methods, such as the FDK method well-known to those skilled in the volume image reconstruction arts.

An optional partial scan compensation step S150 is then executed when it is necessary to correct for constrained scan data or image truncation and related problems that relate to positioning the detector about the imaged subject throughout the scan orbit. A ramp filtering step S160 follows, providing row-wise linear filtering that is regularized with the noise suppression window in conventional processing. A back projection step S170 is then executed and an image formation step S180 reconstructs the 3-D volume image using one or more of the non-truncation corrected images. FDK processing generally encompasses the procedures of steps S160 and S170. The reconstructed 3-D image can then be stored in a computer-accessible memory and displayed.

Conventional image processing sequence S100 of FIG. 28 has been proven and refined in numerous cases with both phantom and patient images.

Although sometimes described herein with respect to CBCT digital radiography systems, embodiments of the application are not intended to be so limited. For example, other DR imaging system such as dental DR imaging systems, mobile DR imaging systems or room-based DR imaging systems can utilize method and apparatus embodiments according to the application. As described herein, an exemplary flat panel DR detector/imager is capable of both single shot (radiographic) and continuous (fluoroscopic) image acquisition. Further, a fan beam CT DR imaging system can be used.

Exemplary DR detectors can be classified into the "direct conversion type" one for directly converting the radiation to an electronic signal and the "indirect conversion type" one for converting the radiation to fluorescence to convert the fluorescence to an electronic signal. An indirect conversion type radiographic detector generally includes a scintillator for receiving the radiation to generate fluorescence with the strength in accordance with the amount of the radiation.

It should be noted that while the present description and examples are primarily directed to radiographic medical imaging of a human or other subject, embodiments of apparatus and methods of the present application can also be applied to other radiographic imaging applications. This includes applications such as non-destructive testing (NDT), for which radiographic images may be obtained and provided with different processing treatments in order to accentuate different features of the imaged subject.

In one embodiment, a value of the bounding spectral curve is based on the multiplicity of photon emission ray paths transmission values. In one embodiment, intra system components can include an anode spectral emission.

Consistent with at least one embodiment, exemplary methods/apparatus can use a computer program with stored instructions that perform on image data that is accessed from an electronic memory. As can be appreciated by those skilled in the image processing arts, a computer program of an embodiment herein can be utilized by a suitable, general-purpose computer system, such as a personal computer or workstation. However, many other types of computer systems can be used to execute the computer program of described exemplary embodiments, including an arrangement of networked processors, for example.

A computer program for performing methods of certain exemplary embodiments described herein may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. Computer programs for performing exemplary methods of described embodiments may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that can be directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products for exemplary embodiments herein may make use of various image manipulation algorithms and processes that are well known. It will be further understood that exemplary computer program product embodiments herein may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the application, are not specifically shown or described herein and may be selected from such algorithms, systems, hardware, components and elements known in the art.

Exemplary embodiments according to the application can include various features described herein (individually or in combination).

While the invention has been illustrated with respect to one or more implementations, alterations and/or modifications can be made to the illustrated examples without departing from the spirit and scope of the appended claims. In addition, while a particular feature of the invention can have been disclosed with respect to only one of several implementations/embodiments, such feature can be combined with one or more other features of the other implementations/embodiments as can be desired and advantageous for any given or particular function. The term "at least one of" is used to mean one or more of the listed items can be selected. The term "about" indicates that the value listed can be somewhat altered, as long as the alteration does not result in nonconformance of the process or structure to the illustrated embodiment. Finally, "exemplary" indicates the description is used as an example, rather than implying that it is an ideal. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of reconstructing a 3-dimensional volume image of an object captured with an x-ray imaging system having an x-ray source configured to emit x-ray photons and a detector having a plurality of imaging pixels to capture x-ray images of the object, the method comprising:

receiving 3-dimensional volume image data of the object;

identifying components of the x-ray imaging system placed between the x-ray source and the object;

calculating transmission values for a plurality of energy levels of the x-ray source, wherein each energy level is associated with a plurality of x-ray photon paths that pass through the identified components of the x-ray imaging system and impact the imaging pixels;

constructing a bounding spectral curve based on the transmission values, including accepting and rejecting a plurality of simulated x-ray photons using the bounding spectral curve as a threshold;

generating scattered image data based on the step of accepting and rejecting the plurality of simulated x-ray photons; and reconstructing the 3-dimensional volume image of the object using the scattered image data in combination with the captured x-ray images of the object.

2. The method of claim 1, wherein the bounding spectral curve does not correspond to a physically realizable spectrum.

3. The method of claim 1, further comprising constructing the bounding spectral curve to reject less than 20% of the simulated x-ray photons.

4. The method of claim 1, further comprising predicting a primary signal using the bounding spectral curve.

5. The method of claim 1, further comprising generating the 3-dimensional volume image data using projection images of the object captured by the imaging system, and subtracting the scattered image data from the captured projection images.

6. The method of claim 1, further comprising defining the 3-dimensional volume image data of the object using discrete voxels with each voxel comprising a material type and a density value.

7. The method of claim 1, wherein the identified components of the x-ray imaging system comprise at least a filter.

8. The method of claim 1, wherein the components of the x-ray imaging system comprise a bowtie filter or a filter of varying dimensions.

9. The method of claim 1, wherein the step of calculating comprises calculating transmission values only for a plurality of energy levels associated with x-ray photon paths that do not pass through the object whose 3-dimensional volume image is reconstructed.

10. The method of claim 1, wherein the step of receiving includes generating the 3-dimensional volume image data of the object using the x-ray imaging system and wherein the step of identifying includes identifying components of the x-ray imaging system while the x-ray imaging system was generating the 3-dimensional volume image data.

11. The method of claim 1, further comprising reconstructing the 3-dimensional volume image of the object by mathematically combining the scattered image data with the captured x-ray images of the object using weighting, subtraction, or a combination thereof.

12. The method of claim 1, wherein the step of calculating transmission values includes determining an emission angle of the x-ray photon paths.

13. The method of claim 12, wherein the step of constructing the bounding spectral curve comprises selecting a maximum transmission value calculated for each of the plurality of energy levels of the x-ray source.

14. A computer-implemented method of reconstructing a 3-dimensional volume image of an object from projection images of the object captured with an x-ray imaging system that includes an x-ray source to emit x-ray photons and an electronic sensor, the method comprising:

receiving 3-dimensional volume image data of the object;

identifying components of the imaging system placed between the x-ray source and the object;

calculating transmission values for photon energy levels of simulated x-ray photons associated with a plurality of simulated x-ray photon paths passing through only the identified components of the imaging system before impacting the electronic sensor;

constructing a bounding spectral curve based on a function of photon energy levels of the simulated x-ray photons, including using a maximum calculated transmission value for the plurality of simulated x-ray photon paths;

generating scattered image data, including accepting and rejecting a plurality of simulated x-ray photons using the bounding spectral curve as a threshold; and reconstructing the 3-dimensional volume image of the object using the scattered image data and the captured projection images of the object.

15. The method of claim 14, further comprising generating an intensity and spectral shape of the simulated x-ray photons as a function of an emission field angle of the simulated x-ray photons.

16. The method of claim 14, wherein the bounding spectral curve does not correspond to a physically realizable spectrum.

17. The method of claim 14, further comprising constructing the bounding spectral curve to reject less than 20% of the simulated x-ray photons.

18. The method of claim 14, further comprising generating the 3-dimensional volume image data using projection images of the object captured by the imaging system, and subtracting the scattered image data from the projection images of the object.

19. A method of reconstructing a 3-dimensional volume image of an object from projection images of the object captured with an x-ray imaging system that includes an x-ray source to emit x-ray photons and an electronic sensor, the method comprising:

receiving 3-dimensional volume image data of the object generated by the x-ray imaging system;

identifying components of the x-ray imaging system placed before the object while the x-ray system generated the 3-dimensional volume image data;

representing x-ray emission characteristics of the x-ray source as a function of an angle of emission of the x-ray photons and an energy level of the x-ray photons;

simulating a forward projection of the x-ray photons through only the identified components and not through the object before impacting the electronic sensor to generate scattered image data using the x-ray emission characteristics; and reconstructing the 3-dimensional volume image of the object using the captured projection images of the object and the scattered image data.

20. The method of claim 19, further comprising using a cone beam x-ray source to emit the x-ray photons.

* * * * *